(12) United States Patent
Hnasko

(10) Patent No.: US 10,570,172 B1
(45) Date of Patent: Feb. 25, 2020

(54) SELF-ASSEMBLING AMPHIPHILIC PEPTIDES

(75) Inventor: Robert M. Hnasko, Port Costa, CA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 1222 days.

(21) Appl. No.: 12/571,228

(22) Filed: Sep. 30, 2009

Related U.S. Application Data

(60) Provisional application No. 61/101,390, filed on Sep. 30, 2008.

(51) Int. Cl.
*C07K 4/00* (2006.01)
*A61K 33/34* (2006.01)
*A61K 38/03* (2006.01)

(52) U.S. Cl.
CPC .............. *C07K 4/00* (2013.01); *A61K 33/34* (2013.01); *A61K 38/03* (2013.01)

(58) Field of Classification Search
None
See application file for complete search history.

(56) References Cited

U.S. PATENT DOCUMENTS

| 4,806,627 A * | 2/1989 | Wisniewski et al. ...... 530/388.2 |
| 5,955,343 A * | 9/1999 | Holmes et al. ............... 435/325 |
| 2004/0208919 A1 * | 10/2004 | Nicolau et al. ............... 424/450 |
| 2005/0287186 A1 * | 12/2005 | Ellis-Behnke ......... A61K 38/10 424/423 |
| 2006/0063919 A1 * | 3/2006 | Lynn et al. .................... 530/350 |
| 2006/0084607 A1 * | 4/2006 | Spirio et al. .................... 514/13 |
| 2007/0190603 A1 * | 8/2007 | Holmes ................ C07K 5/0815 435/69.1 |

OTHER PUBLICATIONS

Yuan et al., "Detection of prion epitopes on PrPc and PrPsc of transmissible spongiform encephalopathies using specific monoclonal antibodies to PrP", Nature, 2005, 83: 632-637.*
Matzelle et al., Biomaterials, vol. 25, pp. 295-304, 2004.*
Dubois et al., J. Biomed. Mater. Res. Part B: Appl. Biomater., vol. 87B, pp. 222-228, online Apr. 3, 2008.*
Morgan et al, J. Am. Chem. Soc., vol. 124, pp. 12644-12645, 2002.*
Hamada et al., J. Biomed. Mater. Res. Part A, vol. 84A , online Jun. 28, 2007, pp. 128-136.*

* cited by examiner

*Primary Examiner* — Daniel E Kolker
*Assistant Examiner* — Aditi Dutt
(74) *Attorney, Agent, or Firm* — John D. Fado; Mark D. McNemar

(57) ABSTRACT

Self assembling peptides in combination with infectious and non-infectious proteins as inhibitors and diagnostic tools in transmissible spongiform encephalopathies and amyloid producing neuorodegenerative diseases are described herein.

4 Claims, 5 Drawing Sheets

FIG. 1A-D

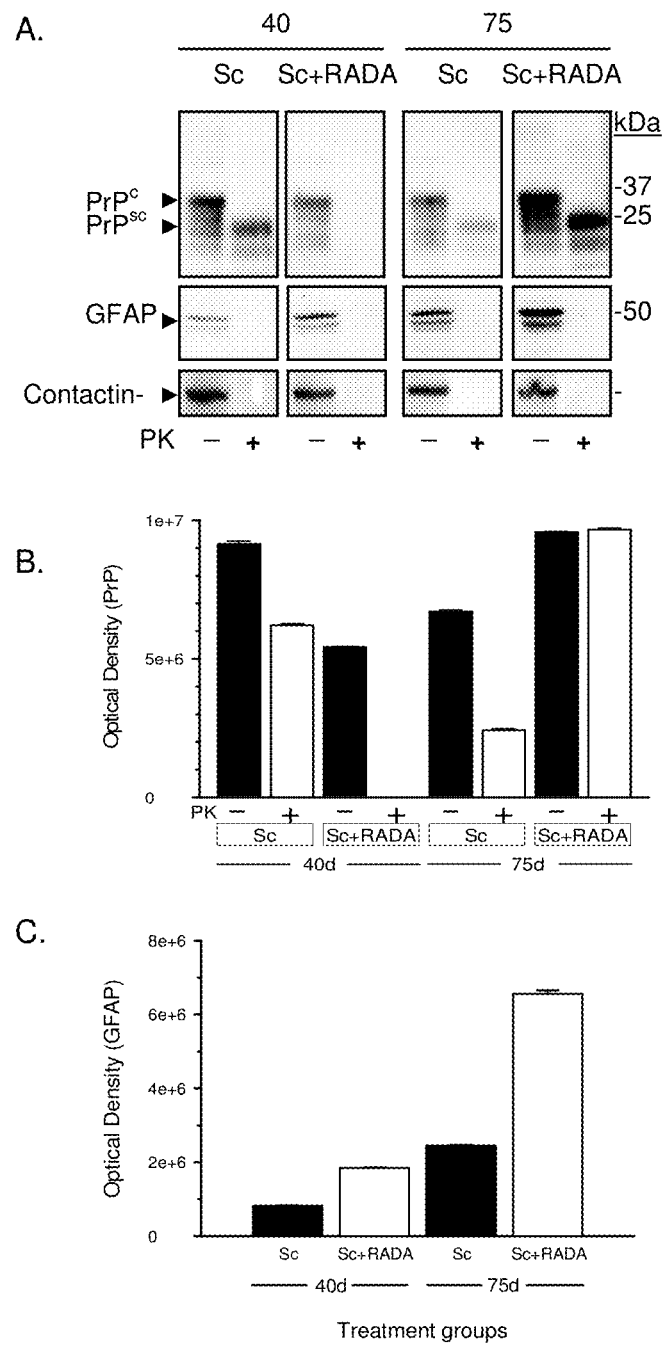
FIG. 3A-C

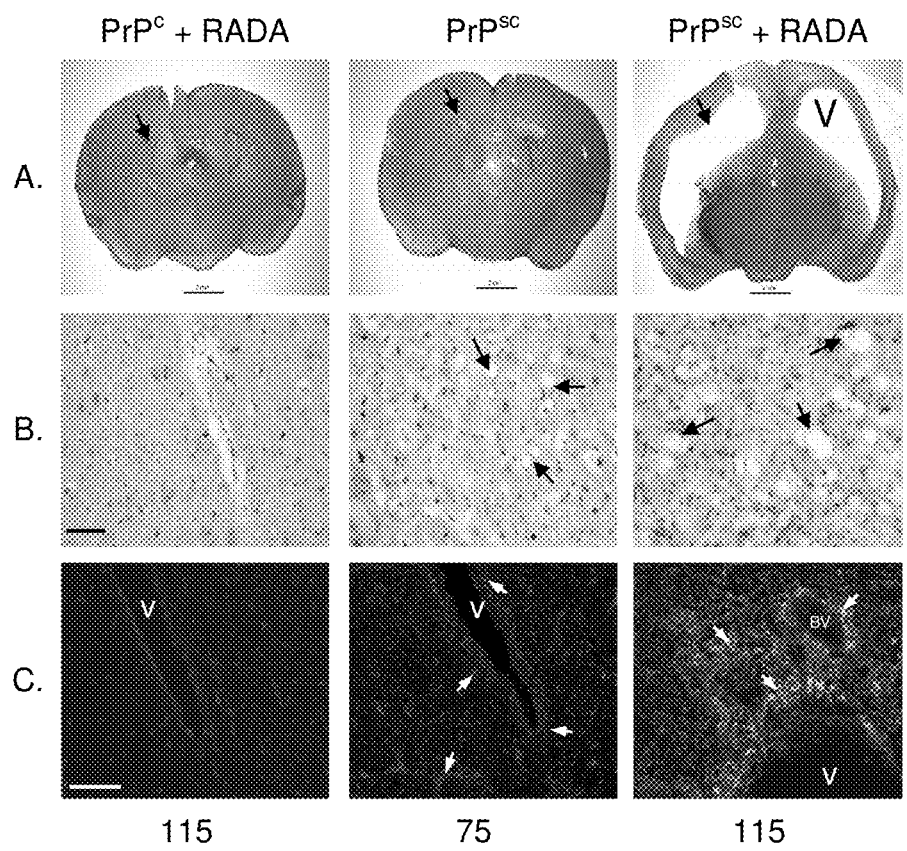
FIG. 4A-C

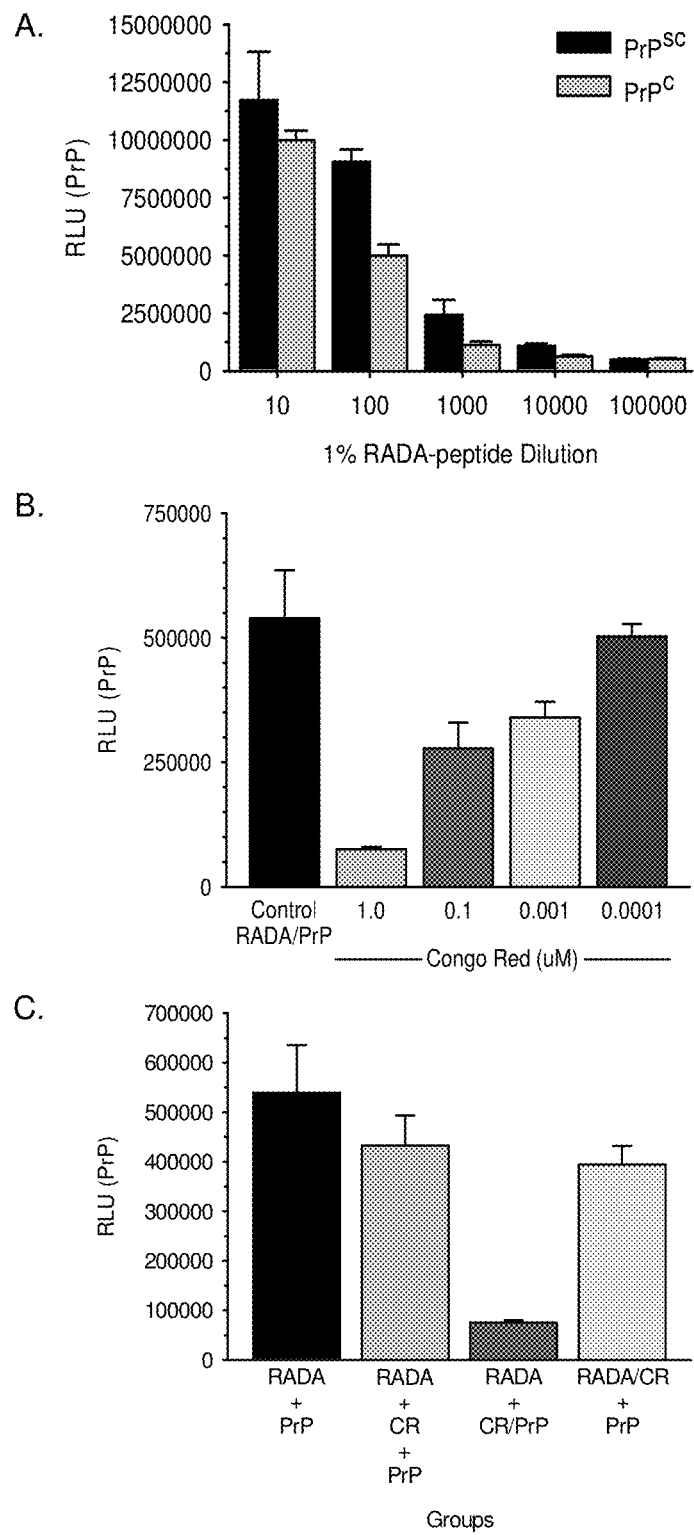
FIG. 5 A-C

SELF-ASSEMBLING AMPHIPHILIC PEPTIDES

RELATED APPLICATIONS

This application claims priority to U.S. Provisional Patent Application Ser. No. 61/101,390, filed Sep. 30, 2008 the contents of which are incorporated herein by reference in their entirety.

FIELD OF THE INVENTION

The present invention relates to self assembling peptides as inhibitors and diagnostic tools in transmissible spongiform encephalopathies and amyloid producing neuorodegenerative diseases.

BACKGROUND OF THE INVENTION

Transmissible spongiform encephalopathies are incurable, fatal neurodegenerative diseases characterized by the accumulation of abnormal prion protein (PrPsc), neuronal cell death and vacuolation of brain tissue. The PrPsc protein is extractable from diseased tissue and is distinguished from endogenous PrPc by partial protease resistance and detergent insolubility. The transmissible agent is the PrPsc protein and it serves as a template for the molecular conversion of endogenous host PrPc into the abnormal PrPsc structural isoform. Host expression of PrPc is necessary for disease transmission, as ablation of the PrPc gene prevents disease whereas the over expression of PrPc followed by PrPsc challenge accelerates disease. The molecular events that mediate neuronal PrPc to PrPsc conversion, not simply accumulated PrPsc, appears to be the initiating factor mitigating the neurodegenerative disease process.

The emergence of robust animal, cellular and biochemical models of prion disease has prompted the evaluation of a wide array of chemical agents targeted for use in therapeutic treatment (10-12). Yet, none have proven clinically effective with only a few chemical compounds identified that can delay the onset of prion disease in animal models (13). The only effective prevention of prion disease has been achieved by ablation or knockdown of PrPc in transgenic animals (14, 15). Alternate approaches such as protein based strategies have focused primarily on immunomodulation (16-18), or in one study, a PrPc-derived beta-sheet breaker peptide was shown to disrupt PrPsc structure and shown to delay the onset of clinical disease in mice (19).

The use of synthetic peptides designed with intrinsic functional protein domains have been engineered to facilitate drug delivery (20), cell attachment (21), and tissue regeneration (22, 23). These biomolecular scaffolds exploit the molecular properties of natural protein sequences to mediate targeted cellular events (22, 24, 25). They offer distinct advantages over traditional pharmacotherapies because they are composed of normal biological constituents, devoid of animal contaminants, biodegradable and do not provoke immune or inflammatory responses (24, 26, 27). Moreover, some of these substrates can mimic the dynamic structural changes observed in protein mis-folding diseases (28-30). The use of these peptides to inhibit endogenous protein mis-folding by protein stabilization, competition, increased clearance or degradation may prove useful in the elucidation of molecular conversion events or therapeutic intervention.

Herein is described a self-assembling synthetic peptide composed of a 16-mer RADA repeat that significantly extends hamster survival when pre-incubated with 263K Scrapie prior to intracerebral inoculation. The RADA-peptide (RADA) forms a hydrated scaffold of beta-sheet nanofibers that supports cell attachment and differentiation (29, 31). We show an initial delay in the accumulation of PrPsc in brain of animals inoculated with RADA followed by a significant increase in total PrPsc by day 75 and at the time of sacrifice. We demonstrate dose-dependent binding of PrP with RADA and show that this interaction can be competitively inhibited with Congo red. The combined inoculation of RADA with PrPsc results in a delay in clinical Scrapie symptoms and significantly extends animal survival. We postulate that a physiochemical interaction of PrPsc with RADA results in a molecular complex that alters PrPsc distribution and thereby impedes the efficacy of prion transmission and disease progression.

SUMMARY OF THE INVENTION

Compositions containing charged amphiphilic peptides that self-assemble into a beta-sheet structures combined with peptides derived from prion and other amyloid forming proteins involved in protein mis-folding diseases; as well as compositions containing amphiphilic peptide sequences with modified amino acids are described herein.

Methods of treating neurodegenerative diseases via administration of compositions containing charged self assembling amphiphilic peptides that actively targets, destabilizes and promotes clearance of aggregate beta-sheet amyloid deposits as well as promote immunomodulatory response that facilitate the degradation and clearance of amyloid are also disclosed.

Diagnostic kits useful in prion detection and depletion assays; probe for diagnostic imaging of amyloid deposits in brain and other organs; and novel immunogen for antibody generation are also described.

BRIEF DESCRIPTION OF THE DRAWINGS

FIG. 1A compares hamster survival in days (mean±SEM) following intracerebral inoculation with 1% Scrapie alone (PrPsc), Scrapie pre-incubated with 0.9% w/v RADA (PrPsc+ RADA) or Scrapie agarose plugs (PrPsc+agarose). FIG. 1B compares hamster survival in days (mean±SEM) with increased dilution of Scrapie brain homogenate alone (open squares) to equivalent doses of Scrapie pre-incubated with 0.9% RADA (open circles). FIG. 1C depicts a hamster survival curve in days (N=6; mean±SEM) with increasing dilution of Scrapie inoculant (open circles). Plotted on the curve (open square) is the mean survival in days of hamsters inoculated with 10-2 Scrapie combined with 0.9% RADA depicting equivalent titer of Scrapie inoculum. FIG. 1D shows a dose-dependent increase in hamster survival in days (mean±SEM) with increasing concentration of RADA (open circles) inoculated with 1% Scrapie.

FIG. 3 (A-C) is a plot of Time-dependent increase in GFAP and PrP protein in hamsters inoculated with combined Scrapie+RADA. FIG. 3A shows a Western blot from hamster brain homogenates inoculated with 1% Scrapie alone (Sc) or combined with 0.9% RADA (Sc+RADA) at 40 d and 75 d treated with (+) or without (-) proteinase-K (PK). The top panels show PrPc and PrPsc detection at each time point (20 μg). Middle panels show detection of GFAP protein and bottom panel contactin-1. FIG. 3B shows quantification of total PrP (−PK) and prion (+PK) from Western blots at each time-point. FIG. 3C show quantification of ~55 kDa GFAP band (−PK) from Western blots from each time-point.

FIG. 4. (A-C) is a photo of the combined inoculation of Scrapie+RADA results in ventricular enlargement, spongiform degeneration, increased gliosis, and large PrPsc aggregates. PrPsc+RADA treatment results in abundant and strong detection of GFAP-positive glia and PrP deposits (green, arrows). V=ventricle. BV=blood vessel. DAPI nuclei (blue). Bar=75 μm.

FIG. 5. (A-C) is a plot of PrP binding RADA-peptide and inhibition with Congo red. FIG. 5A shows chemiluminescent detection of PrP binding to RADA dilutions from Scrapie (PrPsc) and normal (PrPc) brain homogenates. FIG. 5B shows quantification of PrP binding to RADA (Control RADA/PrP) following pre-incubation with dilutions of Congo Red. FIG. 5C compares the binding of PrP to RADA based on the order of reagent addition. RLU=relative light units.

DETAILED DESCRIPTION OF THE INVENTION

Figure 1:
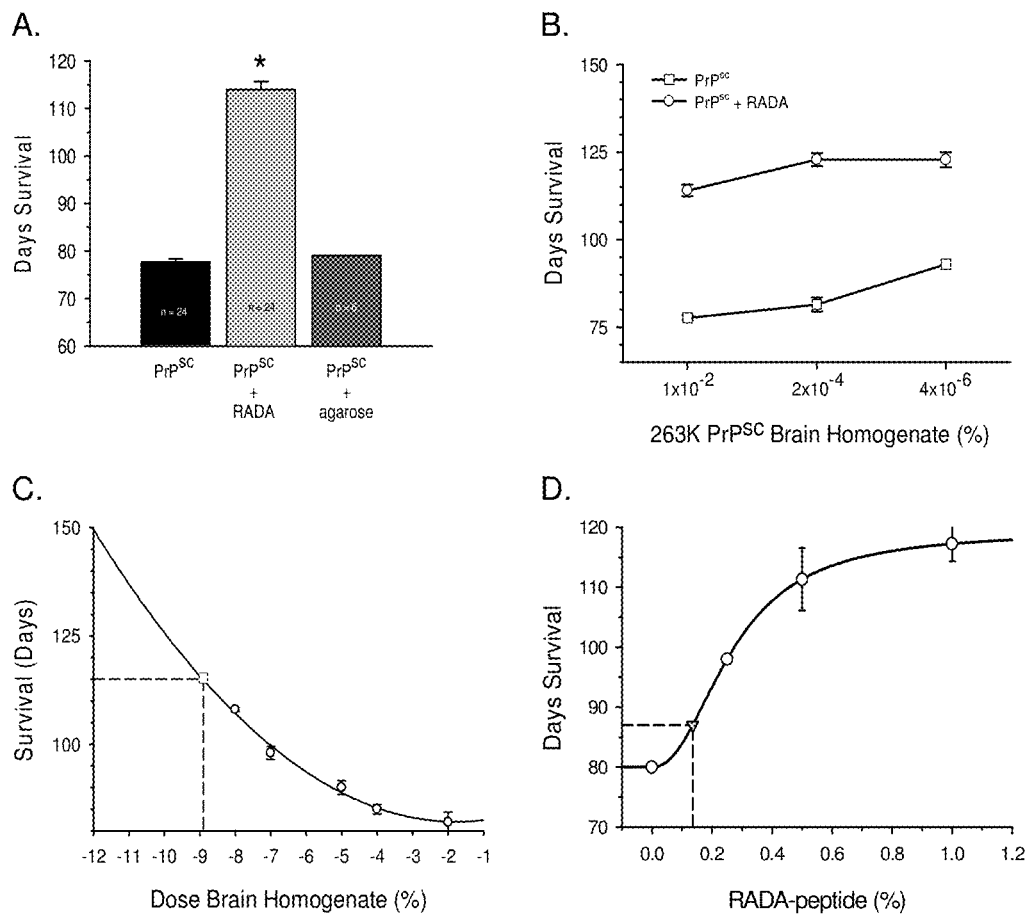
FIG. 1. (A-D) is a graph of RADA promoted increased survival of hamsters inoculated with 263K Scrapie.
Figure 2:
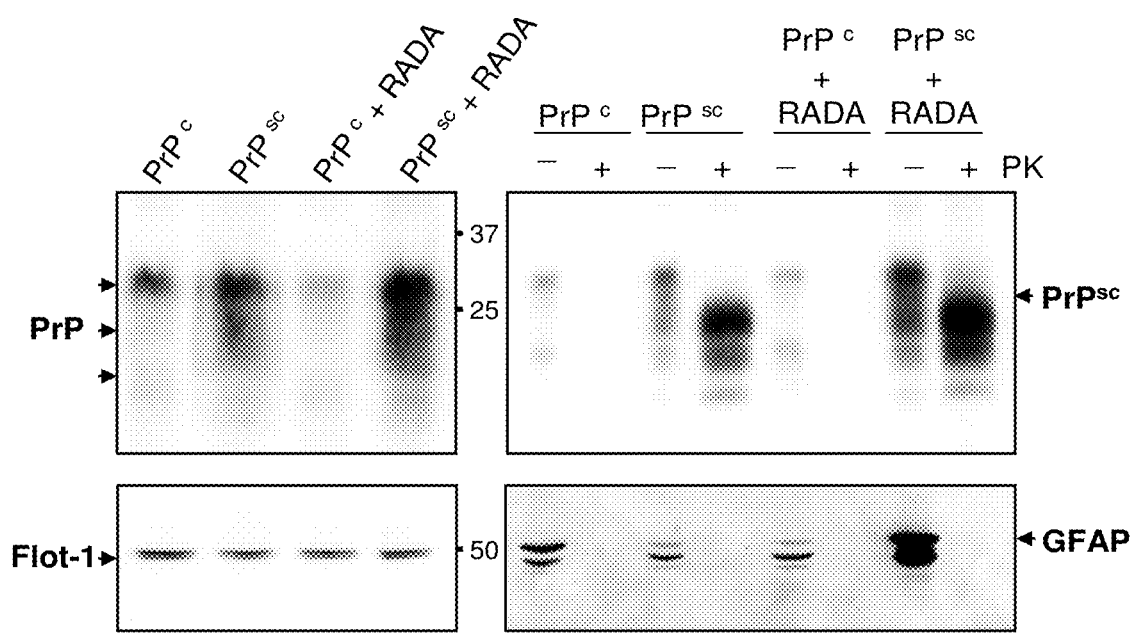
FIG. 2 is a Western blot of increased Prion and GFAP proteins in brain homogenates from hamsters inoculated with Scrapie+RADA.

The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurement.

Definitions

"Effective amount", in reference to an active agent such as a self-assembling peptide or biomolecule, pharmaceutical agent, etc. refers to the amount necessary to elicit a desired biological response. As will be appreciated by those of ordinary skill in this art, the effective amount of an agent may vary depending on such factors as the desired biological endpoint, the agent to be delivered, the nature of the site to which the agent is delivered, the nature of the conditions for which the agent is administered, etc. For example, the effective amount of a composition for treatment of diabetic retinopathy may be an amount sufficient to promote recovery to a greater extent than would occur in the absence of the composition.

"Peptide," as used herein includes "polypeptide," "oligopeptide," and "protein," and refers to a chain of at least two .alpha.-amino acid residues linked together by covalent bonds (e.g., peptide bonds). Useful peptides can vary in length so long as they retain the ability to self-assemble to an extent useful for one or more of the purposes described herein. The number of amino acid residues in the peptide may range from as few as two .alpha.-amino acid residues to about 200 residues. Typically, peptides which self-assemble have from about 6 to about 200 residues, preferably from about 6 to about 64 residues, more preferably from about 8 to about 36 residues, most preferably from about 8 to about 24 residues. The peptides can be at least eight amino acids in length (e.g., eight or 10 amino acids), at least 12 amino acids in length (e.g., 12 or 14 amino acids), or at least 16 amino acids in length (e.g., 16, 18, 20, 22, or 24 amino acids). Peptides that are less than 100 amino acid residues long, more preferably less than approximately 50 amino acids in length, may assemble more readily. In one embodiment, the peptide has from about 8 to about 16 residues. In another embodiment, the peptide has from about 12 to about 20 residues. In yet another embodiment, the peptide has from about 16 to about 20 residues. "Peptide" may refer to an individual peptide or to a collection of peptides having the same or different sequences, any of which may contain naturally occurring .alpha.-amino acid residues, non-naturally occurring .alpha.-amino acid residues, and combinations thereof. .alpha.-Amino acid analogs are also known in the art and may alternatively be employed. In particular, D-.alpha.-amino acid residues may be used.

"Preventing" refers to causing a condition, state, disease, or symptom or manifestation of such, or worsening of the severity of such, not to occur. Preventing includes reducing the risk that a condition, state, or disease, or symptom or manifestation of such, or worsening of the severity of such, will occur.

"Pharmaceutically Acceptable Carrier" refers to a biologically compatible carrier or medium, refers to reagents, cells, compounds, materials, compositions, and/or dosage forms that are not only compatible with the cells and other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio. As described in greater detail herein, pharmaceutically acceptable carriers suitable for use in the present invention include liquids, semi-solid (e.g., gels) and solid materials (e.g., cell scaffolds and matrices, tubes sheets and other such materials as known in the art and described in greater detail herein). These semi-solid and solid materials may be designed to resist degradation within the body (non-biodegradable) or they may be designed to degrade within the body (biodegradable, bioerodable). A biodegradable material may further be bioresorbable or bioabsorbable, i.e., it may be dissolved and absorbed into bodily fluids (water-soluble implants are one example), or degraded and ultimately eliminated from the body, either by conversion into other materials or breakdown and elimination through natural pathways.

A "beta sheet" is secondary structure in proteins consisting of beta strands connected laterally by three or more hydrogen bonds that forms a pleated sheet. A "beta strand" is a stretch of amino acids (typically 5-10) whose peptide backbones are almost fully extended. The formation of protein aggregates and fibrils observed in many human diseases, notably the "amyloidoses" are associated with beta-sheet structures.

"Amyloid" is an insoluble fibrous protein aggregate that may lead to amyloidosis, and is characteristic of neurodegenerative diseases including but not limited to transmissible spongiform encephalopathies (TSEs) and Alzheimer. Amyloid is characterized by a cross-beta sheet quaternary structure in that the beta-strands of the stacked beta-sheets are from different protein monomers and align perpendicular to the axis of the fibril. Amyloid is formed by non-covalent polymerization (self-assembly) and is amino acid sequence-sensitive. Disruption of amyloid polymerization can be accomplished by alterations in amino acid sequences that abrogate ordered beta-sheet stacking.

An embodiment of the invention is a composition containing an amphiphilic peptide that self-assembles into a stable beta-sheet that binds amyloid. Disruption of endogenous amyloid can be accomplished by use of complementary non-pathogenic self-assembling amphiphilic peptides combined with a selective targeting peptide such as those derived from the prion or beta-amyloid proteins. The resulting complex will associate with endogenous amyloids; disrupt further amyloid polymerization, promote de-polymerization of existing amyloid, provide a novel substrate to elicit a beneficial immune response to facilitate degradation and clearance of existing and future amyloid deposits.

A preferred embodiment of the invention is the use of the self assembling peptide RADA-16; when combined with a non-infectious prion or amyloid peptide (ie beta-amyloid) promotes a targeted immune response to aggregate amyloid, forms a beta-sheet structure that targets and disrupts aggregate amyloid (ie. RADApRADA), forms a structure that preferentially binds infectious prion, and uses chiral modification to amino acid composition (D-amino acids) to promote stability and/or the interconversion of two secondary structures (alpha-helix reversible beta-sheet) induced by external conditions such as pH, temperature, concentration, and added components to create amphiphilic switch peptides in aqueous solution. Self assembling beta-sheet peptides such as PURAMATRIX™ as well as other self-assembling peptides discussed in U.S. Pat. Nos. 5,670,483 and 5,955, 343, U.S. Patent Application No. 2002/0160471, PCT Application No. WO02/062969, and U.S. 2006/0084607 may be used. Suitable amphiphilic peptides as discussed but not limited to those in United States 2006/0084607 can be used as well.

Additional modifications to such peptides such as chirl amino acid composition (D-amino acids) and the incremental insertion of proline or glycine residues between amino acid repeats (ie. RADApRADA) to form beta hairpin motifs in which two antiparallel strands are linked by a short loop of one to five proline or glycine residues to assume a dihedral-angle conformation required for a tight turn. Additional components may be combined with the self-assembling amphiphilic peptide that include synthetic peptides or chemical moieties that can adopt a complimentary beta-sheet structure. Peptides derived from prion, beta-amyloid, and other proteins involved with amyloidosis, transmissible spongiform encephalopathies (TSEs), and Alzheimer's disease.

The amphiphilic peptide compositions may be used as a therapeutic agent; to elicit an beneficial immune response, disrupt amyloid formation, promote amyloid degradation and clearance as a means of prevention or treatment of disease states resulting from the presence or conversion of normal prions to abnormal prions; as well as protein misfolding diseases arising from the accumulation of abnormal amyloid aggregates associated with endogenous factors or complements thereof, including but not limited to the infectious prions such as those responsible for Scrapie, Chronic Wasting Disease (CWD) prion, Bovine Spongiform Encephalopathy (BSE) prion, Creutzfeldt-Jakob Disease (CJD) prion, Variant Creutzfeldt-Jakob Disease (vCJD), new Variant Creutzfeldt-Jakob Disease (nvCJD) Gerstmann Straussler-Scheinker syndrome (GSS) prionFeline Spongiform encephalopathy (FSE) prion, Exotic ungulate encephalopathy (EUE) prion.

A preferred embodiment is the use of a composition containing RADA16 and non-infectious prion peptides that alone or with the addition of exogenous factors, such as metal ions, adopt a complimentary beta-sheet structure that promotes RADA16 binding for use in the treatment of transmissible spongiform encephalopathies. The metal ions include but are not limited to $Cu^{2+}$ ions (copper sulfate or copper chloride solution at 0.1-10 mM).

An embodiment of the invention is a method of treating diseases associated with the infectious prions set forth above via administration of compositions containing amphiphilic peptides that self assemble into beta-sheet rich filaments that are combined with associated prion or amyloid peptides to: a) targets existing aggregate amyloid deposits disrupting amyloid structure to promote degradation and clearance, b) impedes the formation of new amyloid aggregates, and c) promotes immune response to aggregated amyloid that facilitates degradation of existing deposits and prevents newly formed abnormal amyloid. Intraveous administration of combined amphiphilic amyloid peptide complex would be suitable for treatment of acute disease states rapidly targeting amyloid deposits abundant in the neurovascular blood vessels. This composition is well suited as a therapeutic agent as both the amphiphilic and amyloid peptides are synthetically derived, devoid of animal contaminants, composed of natural amino acid products that are biodegradable. Additionally, intramuscular or intradermal inoculation may be used to elicit an immune response to pathogenic amyloid.

The therapeutic composition may be produced by combining soluble amyloid peptides with 0.01-3% amphiphilic peptide in a pharmaceutically acceptable carrier.

Another embodiment of the invention is the use of self assembling beta-sheet amphiphilic peptides as a matrix for the isolation and enrichment of amyloid proteins such as infectious prions useful in diagnostic assay development and detection. A diagnostic kit composed of the amphiphilic peptide matrix may be used for the capture, enrichment and subsequent detection of infectious prions or other amyloid proteins. The amphiphilic peptide at concentrations sufficient to form a hydrated filamentous scaffold (0.05-3%) may be packed in a chromatographic column with a porous sieve, attached to plastic, or added directly to tubes/plates and isolated from samples by centrifugation.

Another embodiment of the invention is the use of self assembling beta sheet amphiphilic peptides as a matrix or kit that may be used to deplete biological samples such as blood of infectious prions and/or aggregate amyloid proteins.

A further embodiment of the invention is the use of the self assembling amphiphilic peptide as an in vivo amyloid imaging probe. The beta-sheet amphiplic peptide interacts with endogenous aggregate amyloid products, a common product in many neurodegenerative diseases and can therefore be applied as diagnostic imaging probes with the potential to rapidly determine the extant of cerebral prion/amyloid deposits and monitor time dependent changes in amyloid accumulation. Amphiphilic peptides are easily labeled with therapeutic dyes, may be intravenously injected, allowed to bind to existing amyloid in the brain and visualized by conventional technologies for assessment or treatment of disease.

A further embodiment of the invention is the use of the self assembling amphiphilic peptide combined with infectious prion protein amyloid obtained from biological sources for the generation of antibodies against the infectious prion isoform. Currently, no antibodies that specifically recognize the infectious prion isoform have been generated. The primary amino acid sequences of normal and infectious prion are identical with differences only in secondary structure. The primarily alpha-helical structure of normal PrP is sensitive to enzymatic degradation by proteinase-K (PK), whereas infectious prion (beta-sheet rich) is not. No preparation of infectious prion immunogen has proven sufficiently novel to generate antibodies that can directly distinguish it from normal PrP without Proteinase-K pre-treatment. Prion can be enriched from infected brain homogenate and proteinase-K (PK) used to enzymatically remove contaminating proteins including endogenous non-infectous PrP protein (25 ug protein digested 1 h at 60 C with 15 ug/ml PK). The combined amphiphilic peptide/PK-resistant prion immunogen with or without added adjuvant provides a unique platform for prion antigen presentation and would be administered using repeated intraperitoneal injection in mice, rabbits or other suitable animals. Monoclonal antibodies would be generated by fusion of spleen cells from immunized mice with hybridoma cells and cell supernatants screened for production of antibodies against prion protein, amphiphilic peptide or both using ELISA or Western blot. Isolated hybridoma cells producing relevant antibody would used to make ascites and antibodies purified by protein-A affinity. Polyclonal antibodies would be obtained from serum of immunized animals, IgG's isolated by protein-A and screened as described above. A comparative antibody screening strategy such as that which evaluates normal non-infected or recombinant non-PK treated PrP protein with PK-digested prion infected material would be utilized. Antibodies that positively detect the PK-resistant prion infected sample with no detection of normal or recombinant PrP are selected. Additional confirmation of prion specific antibodies may be achieved by immuno-precipitation of infectious prion using the isolated antibodies linked to agarose beads and captured prion protein eluted and biochemically evaluated. Further characterization would be performed with available antibodies that recognize both normal and infectious prion for comparison as well as protein identification methods such as mass spectrometry. The combined amphiphilic-prion amyloid complex represents a novel immunogen that may provide the structural refinement for antigen presentation necessary to generate antibodies to the infectious prion isoform that would be useful in prion diagnostics and disease treatment.

EXAMPLES

Animals:

Female Syrian Golden hamsters (LVG) at 4 weeks of age were housed in pairs on a 12 h light-dark cycle. Animals were provided continual access to food and water. All protocols were approved by the USDA animal care and use committee and experimental procedures conducted in certified BL2 laboratory facility. PrPsc-infected hamsters were sacrificed when clinical Scrapie symptoms included; increased startle response, ataxia, and >5 s righting reflex.

Reagents:

Infectious 263K Scrapie was propagated by serial passage in hamster brains for 72 days following intracerebral inoculation. Infected or normal brains were weighed, frozen on dry ice and stored at −80 C until use. A 16-mer RADA peptide hydrogel was purchased from BD Bioscience as PURAMATRIX™ (Product #354250; Lot #425714) or synthesized to 95% purity (AnaSpec, CA) for comparison. Congo red (Sigma-Aldrich, MO) was solubilized in water at 1 mM. Ultra pure low melting temperature agarose (AquaPor LM, National Diagnostics, GA) was dissolved in water at 65 C and combined with brain homogenate to form agarose plug controls.

Inoculation:

Hamster brain homogenates (10%) were prepared by homogenization in 320 mM sucrose and pre-cleared by centrifugation at 3000 RPM for 10 min at 4 C. Resulting supernatant was processed for inoculation by 1:10 dilution in 320 mM sucrose or PURAMATRIX™ (1% w/v synthetic 16-mer RADA peptide hydrogel) to yield a 1% brain homogenate (dose equivalent $10^{-2}$) in 0.9% peptide hydrogel. Additionally, brain homogenate or PURAMATRIX™ was serially diluted in 320 mM sucrose and final concentration of brain homogenate was achieved by 1:10 dilution in PURAMATRIX™. Samples were vortexed and incubated at room temperature for 20 min prior to unilateral intracerebral inoculation (40 μl) using a 27-gauge needle attached to a 1 ml syringe.

Western Blotting:

Hamster brain homogenates were processed by homogenization in a MES buffer (25 mM MES, 150 mM NaCl, 60 mM n-octyl-glucoside and 1% Triton X-100, pH 6.5) at 4 C and protein concentration quantified by BCA assay (Pierce, IL). Proteinase-K treatment of 25 μg protein was performed at 60 C for 1 h at a final concentration of 15 μg/ml followed by heat denaturation in sample buffer. Equal concentration of protein (20 μg) were loaded on 4-12% polyacrylamide gels and subjected to electrophoresis, transferred to nitrocellulose and probed with anti-PrP mAb IPC1 at 1:10K (Sigma-Aldrich), rbt-a-GFAP 1:5K (Novus, CO), gt-a-flotillin-1 at 1:1K (H-104; Santa Cruz, Calif.) or gt-a-contactin-1 at 1:200 (S-20; Santa Cruz). Corresponding secondary antibodies were used; gt-a-m-HRP (Pierce, IL), gt-a-rbt-HRP (Pierce), or dnk-a-gt-HRP (Jackson, PA) at 1:10K and blots resolved by ECL (Supersignal Pico, Pierce) and imaged on Flurochem HD documentation system (Alpha Innotech, CA).

ELISA Assay:

RADA-peptide hydrogel was diluted in 0.1M sodium bicarbonate buffer (pH 8.6) and adsorbed to black 96-well Maxisorb plates (Nunc, NY) at 4 C overnight. Plates were washed (ELx-405 auto plate washer; Bio-Tek, VT) in TBS with 0.1% Tween-20 (TBST), blocked with 10% non-fat dry milk followed by incubation with dilutions of hamster brain homogenate at 4 C for 18 h. Plates were washed, blocked a second time and incubated with m-a-PrP (mAb IPC1; 10K) diluted in TBST with 0.1% IgG-free BSA (Jackson) followed by gt-a-m-HRP (1:10K) for 1 h. Plates were resolved by ECL (Supersignal Femto, Pierce) and chemiluminescence detected using a Wallac Victor II (PerkinElmer, MA).

Immunofluorescent Microscopy:

Hamster brains were fixed in 10% neutral buffered formalin 72 h at 4 C, sunk in 30% sucrose and 5 μm coronal cryosections collected on glass slides. Sections were washed in 10 mM PBS (pH 7.2) with 0.1% Triton-X100, blocked (Superblock, Pierce) and incubated with m-a-PrP (IPC1, 1:1K) or rbt-a-GFAP (1:1K) diluted in PBST-BSA for 2 h. Alexa Fluor-568 gt-a-ms-IgG or Alexa Fluor-488 gt-a-rbt-IgG (Molecular Probes-Invitrogen, CA) diluted 1:1500 in PBST-BSA containing DAPI and incubated 1 h. Coverslips were applied with ProLong gold anti-fade reagent (Molecular Probes) and imaged using a Leica SP5 confocal microscope equipped with AOTF/AOBS and blue Argon, Yellow DPSS (561 nm) and 405 nm lasers (Leica, Germany).

Histochemistry:

Hamster brains were fixed and thick coronal sections were cut (1 mm) using a steel hamster brain matrix (EM sciences) and gross morphology imaged using a Leica EZ4D stereo microscope. Thin 5 μm cryosections were collected as described and stained with hematoxylin followed by Modified Puchtler's Congo Red (Biocare Medical, CA), sections were dehydrated in graded-ETOH, cleared in Xylene and coverslipped using DPX (EM sciences). Sections were imaged using a Leica DMI400B with an attached DFC320 R2 digital camera.

Statistics:

Sigma Stat software was used for statistical analysis (Systat, CA). Kruskal-Wallis one way analysis of variance on ranks was used followed by pairwise comparison using Mann-Whitney U Rank Sum Test. Post hoc multiple comparisons versus control group (Dunn's or Holm-Sidak method) was also utilized (P<0.05).

Example 1

Increased Survival Time in Animals Inoculated with PrPsc and RADA-Peptide.

Hamsters inoculated with RADA-peptide (RADA) combined with PrPsc survived significantly longer than those that received an equivalent dose of PrPsc alone. The mean survival time of animals inoculated with 1% PrPsc ($10^{-2}$ dose) combined with 0.9% RADA was 114 d (n=24) as compared to 78 d (n=24) for animals that received equivalent PrPsc alone or 80 d (n=6) for animals inoculated with PrPsc-agarose plugs (FIG. 1A; P<0.001). A rapid toxicity was observed with this combined inoculum in 21% of the hamsters within 24 h. This toxicity did not occur in animals that received equivalent doses of PrPsc alone, PrPsc combined with agarose, RADA alone, or normal brain homogenate combined with RADA. With increased dilution of PrPsc+RADA there was reduced morbidity in that 24 h period. No animals died unexpectedly after this initial 24 h period.

As expected, increased dilution of PrPsc resulted in a dose-dependent increase in survival time (FIG. 1B; squares). Importantly, increased dilution of PrPsc with 0.9% RADA resulted in a significant increase in survival time as compared to the equivalent doses of PrPsc alone (FIG. 1B; circles; Mann-Whitney P<0.01). The combined inoculum showed dose-dependence, but a plateau in total survival time (~125 d) was observed at dilutions of PrPsc below $2 \times 10^{-4}$, suggesting that maximal survival promoted by RADA had been achieved. Based on our survival curve for titrated 263K Scrapie (FIG. 1C; open circles; n=6 each data point) the initial PrPsc inoculum of $10^{-2}$ when combined with RADA was equivalent to a starting inoculum of $10^{-9}$ PrPsc alone, a 7-log reduction in prion titer (FIG. 1C; dashed line). In all groups inoculated with PrPsc, clinical Scrapie symptoms (startle response followed by increased righting reflex and ataxia) began 10-15 d prior to sacrifice (data not shown). No animals injected with RADA alone or combined with normal brain homogenate exhibited Scrapie symptoms and those not sacrificed as age-matched controls survived >200 days.

Example 2

Increased Survival is RADA-Peptide Dose-Dependent.

Increased survival time of hamsters inoculated with PrPsc was RADA dose-dependent. When RADA concentration was varied 0-1% with a constant $10^{-2}$ dose of PRPsc there was a dose-dependent increase in survival time with maximal survival achieved at the highest concentration of RADA used (FIG. 1D; circles). The survival curve was sigmoid suggesting that no additional increase in survival would be achieved with RADA concentrations above 1% when combined with the $10^{-2}$ PrPsc dose. We synthesized our own 16-mer RADA-peptide to 95% purity and estimated the concentration of our preparation to be ~0.2% w/v. This material when combined with PrPsc increased survival to ~87 d from 80 d compared to PrPsc alone (Mann-Whitney; P=0.02) and RADA concentration calculated from our survival curve was ~0.14% (FIG. 1D; triangle).

Example 3

Total PrP, Prion and GFAP Proteins are Elevated in Brain of Animals Inoculated with PrPsc—RADA.

Western blot showed increased detection of total PrP protein in brain homogenate of animals that received combined PrPsc with RADA (FIG. 2, top left panel) at the time of sacrifice. Both PrPsc alone and PrPsc combined with the RADA had increased PrP protein compared to animals treated with normal brain homogenate (PrPc). This increase in total PrP is a measure of both PrPc and accumulated PrPsc. The highest level of PrP was detected in brain homogenates from animals treated with PrPsc combined with RADA. Protein load was normalized by BCA and confirmed by detection of the lipid raft marker flotillin-1 which remained unchanged (FIG. 2; bottom left panel). As expected, PrP from hamsters inoculated with control brain homogenate, either alone (PrPc) or in combination with RADA (PrPc+RADA), were proteinase-K (PK) sensitive (FIG. 2, top right panel). Brain homogenates from hamsters inoculated with PrPsc alone (PrPsc) or combined with RADA (PrPsc+RADA) had detectable PK-resistant prion, with the greatest amount detected in brain homogenate from animals that received the combined inoculant (FIG. 2, top right panel). Glial fibrillary acidic protein (GFAP) was used to validate the fidelity of the PK reaction and is completely digested by PK in all groups (FIG. 2, bottom right panel). Interestingly, more detectable GFAP protein was present in brain homogenate from the animals that received PrPsc+RADA (FIG. 2, bottom right panel).

Example 4

Delayed PrPsc Accumulation with RADA-Peptide.

In contrast to animals that received inoculation of PrPsc alone, no PK-resistant prion was detected by Western blot in brain homogenates at 40 d from animals that received PrPsc+RADA (FIG. 3A; top panels; left side). At 75 d the animals that received PrPsc alone had late stage clinical Scrapie symptoms whereas those that received PrPsc with RADA had no observable symptoms (data not shown). At the 75 d time point PK-resistant prion was detected in brain of animals that received PrPsc alone or combined with RADA (FIG. 3A; top panel; right side). Detection of GFAP protein by Western blot increased from day 40 to 75 in animals of both treatment groups (FIG. 3A; middle panels), but was greater in brains of animals that received PrPsc+RADA at both time points (FIG. 3C; $P<0.001$). Protein load was normalized by BCA and confirmed by the equal and unchanged detection of the GPI-anchored contactin-1 protein which also served to validate PK digestion (FIG. 3A; bottom panels). Quantification of Western blots shows at 40 d there is significantly more PK-resistant prion protein in animals inoculated with PrPsc alone (FIG. 3B; P<0.001), whereas at 75 d there is significantly more prion protein in brain homogenate from animals inoculated with PrPsc+ RADA (FIG. 3B; P<0.001).

Example 5

Ventricular Enlargement, Amyloidosis and Spongiform Degeneration.

At the time of sacrifice the brains of hamsters inoculated with PrPsc+RADA were filled with an increased amount of cerebral spinal fluid (CSF) compared to animals inoculated with PrPsc alone, however gross wet weight (~1 g) did not differ significantly between these treatment groups (data not shown). Coronal sections show massive enlargement of the lateral ventricles in brains from animals that received PrPsc+ RADA relative to those inoculated with PrPsc alone (FIG. 4A; top panels). Cryosections counterstained with hematoxylin and Congo red were evaluated for amyloid deposits and spongiform degeneration. Negative control sections collected from animals inoculated with normal brain homogenate combined with RADA (115 d) showed no detectable Congo Red amyloid deposits nor spongiform degeneration (FIG. 4B; middle left panel). Sections from hamsters inoculated with PrPsc alone (75 d) showed detectable Congo red positive amyloid in blood vessels (data not shown) and typical spongiform degeneration of brain (FIG. 4B; middle center panel; arrows). Brain sections from animals that received PrPsc+RADA (115 d) showed a similar histological pathology as PrPsc alone that included prototypical spongiform degeneration (FIG. 4B; middle right panel; arrows).

Example 6

Increased Immunoreactive GFAP and PrP Proteins in Brain Following PrPsc Inoculation with RADA-Peptide.

Hamster brain sections from animals at the time of sacrifice showed increased immunoreactive GFAP positive glia in brains inoculated with PrPsc alone (day 75) or PrPsc combined with RADA (day 115) as compared to animals inoculated with normal brain homogenate and RADA (FIG. 3C). Few GFAP immunoreactive astrocytes were detectable at 115 d in control brain (RADA alone) and PrP was undetectable by immunofluorescence (FIG. 3C; left panel). Animals that received PrPsc alone showed increased GFAP positive astrocytes with some detectable PrP protein (FIG. 3C; middle panel; white arrows). Animals that received PrPsc+RADA showed a massive increase in immunoreactive GFAP and large PrP deposits (FIG. 3C; right panel; white arrows). These immunoreactive PrP-positive aggregates were PK resistant (data not shown).

Example 7

PrP Binds RADA-Peptide and Binding is Inhibited by Congo Red.

Normal and Scrapie-infected brain homogenates were incubated with RADA bound to 96-well plates. PrP binding was dependent on the concentration of RADA with no significant difference observed between normal or Scrapie brain (FIG. 5A). Pre-incubation with Congo red resulted in a dose-dependent inhibition of binding of PrP to RADA with a significant inhibition of PrP binding observed at 1 uM Congo red (FIG. 5B; Mann-Whitney; p>0.001). Importantly, the inhibition of PrP binding to RADA by Congo red was dependent on the order of reagent addition; inhibition required Congo red pre-incubation with PrP prior to RADA exposure (FIG. 5C). RADA pre-incubated with Congo red before or after plate binding was ineffective in inhibiting the binding of PrP, suggesting that the Congo red interacts with PrP, not RADA, to inhibit binding.

Example 8

PrPsc Infectivity is not Modified by RADA-Peptide.

We used four independent preparations of RADA combined with PrPsc to show increased survival time in hamsters was not limited to a single sample. All treatment groups showed a significant increase in animal survival compared to those inoculated with equivalent dose of PrPsc alone. Moreover, when brain homogenate was prepared from animals inoculated with PrPsc combined with RADA and re-inoculated back into a new group of hamsters (PrPsc/RADA; dose $10^{-2}$) no increase in survival was observed. This demonstrates that the property of Scrapie infectivity was not modified by exposure to the RADA in subsequent passage. The same inoculant when combined with RADA again (PrPsc/RADA+RADA), resulted in an increased survival time.

What is claimed:

1. A composition comprising an amphiphilic peptide that self-assembles into a stable beta-sheet that binds amyloid, a non-infectious amyloid peptide or non-infectious prion, and a pharmaceutically acceptable carrier, wherein the self-assembling peptide is RADA-16.

2. The composition of claim 1, further comprising metal ions that confer a complementary beta sheet structure.

3. The composition of claim 2, wherein the metal ions are $Cu^{2+}$ ions.

4. A method of treating a disease arising from the accumulation of abnormal amyloid aggregates or protein misfolding comprising administration of the composition of claim 1 wherein the disease is selected from the group consisting of Scrapie, Chronic Wasting Disease (CWD) prion, Bovine Spongiform Encephalopathy (BSE) prion, Creutzfeldt-Jakob Disease (CJD) prion, Variant Creutzfeldt-Jakob Disease (vCJD), Gerstmann Straussler-Scheinker syndrome (GSS) prion, Feline Spongiform encephalopathy (FSE) prion, and Exotic ungulate encephalopathy (EUE) prion.

* * * * *